US010912788B2

(12) United States Patent
Wassenaar et al.

(10) Patent No.: US 10,912,788 B2
(45) Date of Patent: Feb. 9, 2021

(54) METHODS AND COMPOSITIONS FOR PREVENTING AND TREATING CONDITIONS RELATED TO ALPHA-SYNUCLEIN

(71) Applicant: PurePharm, Inc., Toronto (CA)

(72) Inventors: Willem Wassenaar, Toronto (CA); Alfonso Fasano, Toronto (CA)

(73) Assignee: PurePharm, Inc., Toronto (CA)

( * ) Notice: Subject to any disclaimer, the term of this patent is extended or adjusted under 35 U.S.C. 154(b) by 71 days.

(21) Appl. No.: 16/295,448

(22) Filed: Mar. 7, 2019

(65) Prior Publication Data

US 2020/0179421 A1     Jun. 11, 2020

Related U.S. Application Data

(60) Provisional application No. 62/640,431, filed on Mar. 8, 2018.

(51) Int. Cl.
| | | |
|---|---|---|
| *A61K 31/7008* | (2006.01) | |
| *A61P 1/10* | (2006.01) | |
| *A61K 31/7072* | (2006.01) | |
| *A61K 35/28* | (2015.01) | |
| *A61K 45/06* | (2006.01) | |

(52) U.S. Cl.
CPC ...... *A61K 31/7008* (2013.01); *A61K 31/7072* (2013.01); *A61K 35/28* (2013.01); *A61K 45/06* (2013.01); *A61P 1/10* (2018.01)

(58) Field of Classification Search
CPC .................................. A61K 31/7008
See application file for complete search history.

(56) References Cited

U.S. PATENT DOCUMENTS

| | | | | |
|---|---|---|---|---|
| 4,474,893 | A | 10/1984 | Reading | |
| 4,816,567 | A | 3/1989 | Cabilly | |
| 5,229,374 | A * | 7/1993 | Burton | A61K 31/7004 514/62 |
| 2016/0123961 | A1* | 5/2016 | Lee | A61K 31/7008 800/3 |

FOREIGN PATENT DOCUMENTS

| | | |
|---|---|---|
| CA | 1318592 C | 6/1993 |
| WO | WO 2016/139330 A1 | 9/2016 |

OTHER PUBLICATIONS

Cansev et al., Neurosci Res., 2008, 62(3): 206-209.*
Thobois's Clin Ther., 2006, 28(1): 1-12 (abstract).*
Adler et al., Submandibular Gland Needle Biopsy for the Diagnosis of Parkinson Disease, Neurology. Mar. 11, 2014;82(10):858-64.
Agachan et al., A Constipation Scoring System to Simplify Evaluation and Management of Constipated Patients, Dis Colon Rectum. Jun. 1996;39(6):681-5.
Barone et al., The PRIAMO Study: A Multicenter Assessment of Nonmotor Symptoms and Their Impact on Quality of Life in Parkinson's Disease, Mov Disord. Aug. 15, 2009;24(11):1641-9.
Cansev et al., Restorative Effects of Uridine Plus Docosahexaenoic Acid in a Rat Model of Parkinson's Disease, Neurosci Res. Nov. 2008;62(3):206-9.
Fahn S, Elton R, Members of the UPDRS Development Committee. Unified Unified Parkinson's Disease Rating Scale, In: Fahn S, Marsden CD, Calne DB, Goldstein M, eds. Recent Developments in Parkinson's Disease, vol. 2. Florham Park, NJ. Macmillan Health Care Information 1987, pp. 15 3-163, 293-30.
Fasano et el., Gastrointestinal Dysfunction in Parkinson's Disease, Lancet Neurol., Jun. 2015;14(6):625-39.
Groves et al., Dynamic O-GlcNAcylation and its roles in the cellular stress response and homeostasis, Cell Stress Chaperones. Sep. 2013; 18(5): 535-558.
Henchcliffe and Beal, Mitochondrial Biology and Oxidative Stress in Parkinson Disease Pathogenesis, Nat Clin Pract Neurol., Nov. 2008;4(11):600-9.
Hurst et al., Assessing the Clinical Significance of Change Scores Recorded on Subjective Outcome Measures, J Manipulative Physiol Ther. Jan. 2004;27(1):26-35.
Jones et al., Replacing the Complementarity-Determining Regions in a Human Antibody With Those From a Mouse, Nature. May 29-Jun. 4, 1986;321(6069):522-5.
Kim et al., Alpha-synuclein Biology in Lewy Body Diseases, Alzheimers Res Ther. Oct. 27, 2014;6(5):73.
Kim et al., Anti-aging Treatments Slow Propagation of Synucleinopathy by Restoring Lysosomal Function, Autophagy. Oct. 2, 2016;12(10):1849-1863. Epub Aug. 2, 2016.
Kim et al., Gastrointestinal Autonomic Dysfunction in Patients with Parkinson's Disease, J Mov Disord. May 2015; 8(2): 76-82.
Marotta et al. O-GlcNAc Modification Blocks the Aggregation and Toxicity of the Protein α-Synuclein Associated With Parkinson's Disease, Nat Chem. Nov. 2015;7(11):913-20. Epub Oct. 12, 2015.
Reichmann et al., Reshaping Human Antibodies for Therapy, Nature. Mar. 24, 1988;332(6162):323-7.
Salvatore et al., A Pilot Study of N-acetyl Glucosamine, a Nutritional Substrate for Glycosaminoglycan Synthesis, in Paediatric Chronic Inflammatory Bowel Disease, Aliment Pharmacol Ther. Dec. 2000;14(12):1567-79.
Seidman et al., Nutritional Modulation of Gut Inflammation. Clinical Nutrition: Early Intervention D. Labadarios; C. Pichard (eds), Nestlé Nutrition Workshop Series Clinical & Performance Program, vol. 7, pp. 41-65, 2002.
Tincello et al., Validation of the Patient Global Impression Scales for Use in Detrusor Overactivity: Secondary Analysis of the Relax Study, BJOG. Jan. 2013;120(2):212-216.
Ueki et al., Life style risks of Parkinson's disease: Association between decreased water intake and constipation, J Neurol. Oct. 2004;251 Suppl 7:vII18-23.
Verhoeyen et al., Reshaping Human Antibodies: Grafting an Antilysozyme Activity, Science. Mar. 25, 1988;239(4847):1534-6.

(Continued)

*Primary Examiner* — Rei Tsang Shiao
(74) *Attorney, Agent, or Firm* — Howson & Howson LLP; Colleen Schaller

(57) ABSTRACT

Provided herein are methods of treating constipation in subjects in need thereof. The method includes administering a therapeutically effective dosage of N-acetylglucosamine. Subjects who may benefit from treatment include those having synucleinopathies, including Parkinson's Disease.

30 Claims, 1 Drawing Sheet

(56) References Cited

OTHER PUBLICATIONS

Viktrup et al., Construct Validation of Patient Global Impression of Severity (PGI-S) and Improvement (PGI-I) Questionnaires in the Treatment of Men With Lower Urinary Tract Symptoms Secondary to Benign Prostatic Hyperplasia, BMC Urol. Nov. 7, 2012;12:30.

Visser et al., Assessment of Autonomic Dysfunction in Parkinson's Disease: The SCOPA-AUT, Mov Disord. Nov. 2004;19(11):1306-12.

Walker et al., Interaction of Human IgG Chimeric Antibodies With the Human FcRI and FcRII Receptors: Requirements for Antibody-Mediated Host Cell-Target Cell Interaction, Mol Immunol. Apr. 1989;26(4):403-11.

Wang et al., Enrichment and Site Mapping of O-linked N-acetylglucosamine by a Combination of Chemical/Enzymatic Tagging, Photochemical Cleavage, and Electron Transfer Dissociation Mass Spectrometry, Mol Cell Proteomics. Jan. 2010;9(1):153-60.

Zhu et al., N-Acetylglucosamine for Treatment of Inflammatory Bowel Disease A real-world pragmatic clinical trial, vol. 7 Issue 4, Apr. 2015.

International Search Report and Written Opinion in International Patent Application No. PCT/CA2019/050276, dated May 28, 2019.

Applicant's submission under Article 34 in support of demand for Chapter II examination in International Patent Application No. PCT/CA2019/050276, dated Jul. 25, 2019.

International Preliminary Report on Patentability in International Patent Application No. PCT/CA2019/050276, dated Apr. 14, 2020.

\* cited by examiner

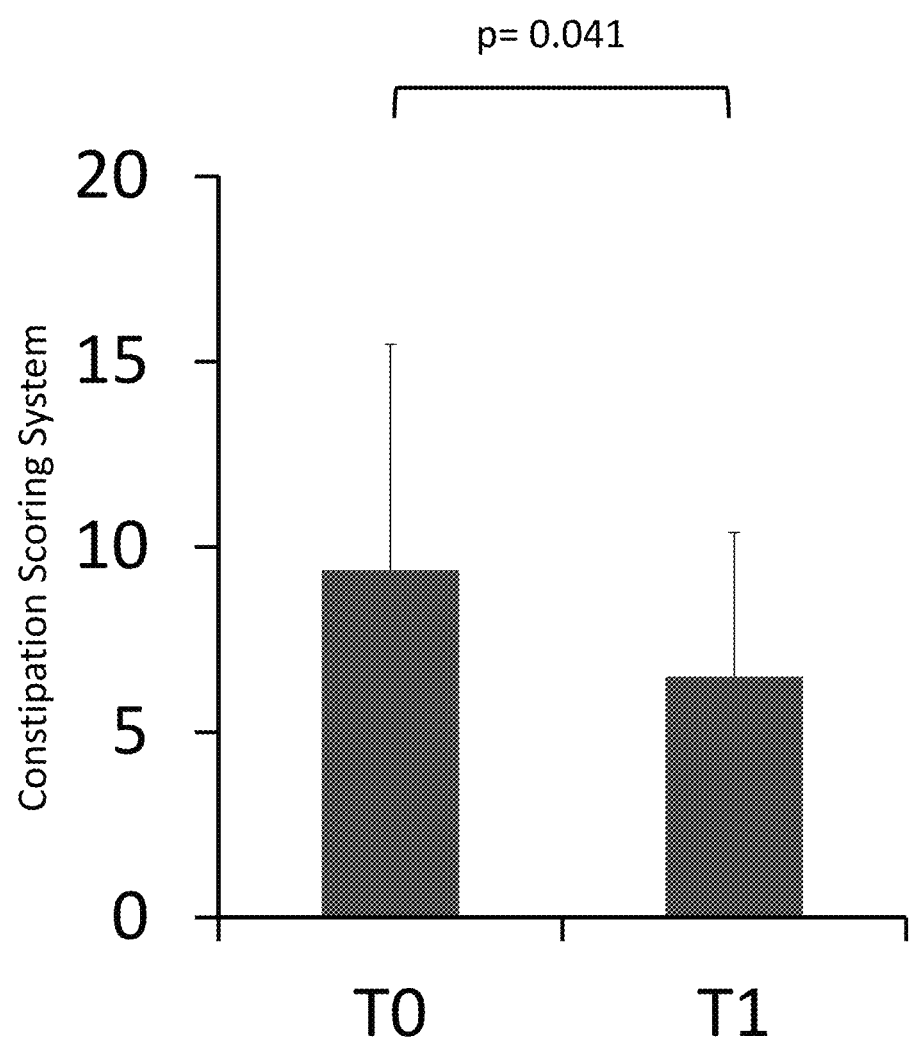

METHODS AND COMPOSITIONS FOR PREVENTING AND TREATING CONDITIONS RELATED TO ALPHA-SYNUCLEIN

N-acetylglucosamine (GlcNAc or NAG) is an amino sugar which plays a role in the synthesis of cellular components, proteoglycans, and maintaining intestinal epithelial barrier function as demonstrated by various preclinical studies. Oral administration of GlcNAc has shown therapeutic efficacy in treating pediatric treatment-resistant inflammatory bowel disease (Crohn's disease and ulcerative colitis patients) by reducing symptoms of gut inflammation and increasing the expression of sulphated glycosaminoglycan (GAG) which promotes proper gut functioning. (Salvatore et al, A pilot study of N-acetylglucosamine, a nutritional substrate for glycosaminoglycan synthesis, in paediatric chronic inflammatory bowel disease, Aliment Pharmacol Ther., 14(12):1567-79 (2000 December), which is incorporated herein by reference).

In addition, in vitro clinical studies have also suggested that post-translational modification of GlcNAc specifically O-GlcNAcylation at threonine residue 72 (Thr72) may have a role in regulating protein folding and inhibiting Parkinson's Disease-associated a-synuclein (aSyn) aggregation. See, Marotta et al, Nat Chem. 2015 November; 7(11): 913-920, which is incorporated herein by reference.

Parkinson's Disease (PD) is a neurodegenerative disease that severely affects dopaminergic neurons, causing various cognitive, motor, and non-motor symptoms such as constipation whose mechanisms are not fully understood but speculated to be in part due to inflammation, dysfunction of the intestinal epithelial barrier, and a vast distribution of alpha-synuclein (α-syn) aggregates in the mucosal plexuses and mucosal nerve fibers. Constipation is one of the most common non-motor symptoms experienced by PD patients and one that often precedes motor symptoms of PD by various years. While studies vary, about 50-80% of patients complain of chronic constipation. In addition, it has also been proposed that delayed colonic transit associated with constipation can prevent complete absorption of levodopa used to treat motor symptoms in PD patients. It has been postulated that anti-aging treatments can slow the progress of synucleinopathies in a C. elegans model of cell-to-cell transmission of SNCA. See, Kim et al, Anti-aging treatments slow propagation of synucleinopathy by restoring lysosomal function, Autophagy, 12(10):1849-63 (2016), which is incorporated by reference herein.

What is needed in the art are effective treatments for PD and other synucleinopathies.

SUMMARY OF THE INVENTION

Provided herein are methods and compositions relating to treatment of synucleinopathies and symptoms thereof. In one aspect, a method of treating constipation in a subject in need thereof is provided. In one embodiment, the method includes administering an effective amount of N-acetylglucosamine or an analog or derivative thereof. In one embodiment, the subject has a synucleinopathy. In another embodiment, the synucleinopathy is selected from Parkinson's Disease, Lewy body dementia, multiple system atrophy (MSA) and pure autonomic failure (PAF).

In another aspect, a method of treating constipation in a subject that does not have a synucleinopathy is provided. In one embodiment, the constipation is a symptom of Crohn's disease, colitis, hypothyroidism, medication, poor diet, pregnancy, diabetes, MS, or a medicinal side effect.

In another aspect, a method of solubilizing alpha-synuclein aggregates in a subject having a synucleinopathy is provided. The method includes administering N-acetylglucosamine or an analog or derivative thereof, wherein motor function in the gut and central nervous system of the subject is normalized.

In another aspect, a method of decreasing alpha-synuclein aggregates in a subject in need thereof is provided. The method includes administering an effective amount of N-acetylglucosamine or an analog or derivative thereof.

Other aspects and advantages of the invention will be readily apparent from the following detailed description of the invention.

BRIEF DESCRIPTION OF THE DRAWINGS

FIG. 1 is a graph showing constipation scoring for patients enrolled in the study described in Example 1. T0 shows constipation score before starting treatment with GlcNAc and T1 shows constipation score after treatment for 1 month.

DETAILED DESCRIPTION OF THE INVENTION

N-acetylglucosamine (GlcNAc), 2-acetamino-2-deoxy-β-D-glucose or 2-(acetylamino)-2-deoxy-D-glucose, is a monosaccharide derivative of glucose and is widely distributed worldwide. The molecular formula of this amino monosaccharide is $C_8H_{15}NO_6$, and its molecular weight is 221.21. In general, it is a white and slightly sweet powder that melts at 221° C. The solubility of GlcNAc is 25% in water, and 1% aqueous solutions are colorless and clear. A pure form of GlcNAc is available under the trade name Villicote®.

In one embodiment of the methods described herein, an analog or derivative of GlcNAc is utilized. Such analogs and derivatives can be generated by the person of skill in the art. The terms analog and derivative may be used interchangeably. Such analogs and derivatives include those which are able to O-GlyNAcylate amino acid residues (serine or threonine) via O-GlcNAc transferase (OGT). Exemplary analogs include, without limitation, streptozotocin and diazirine-modified UDP-GlcNAc (UDP-GlcNDAz). Such derivatives include, without limitation, N-acetylglucosamine 3,6-disulfate, N-acetylglucosamine 3-sulfate, N-acetylglucosamine 6-sulfate, N-acetylglucosamine 1-phosphate, N-acetylglucosamine 6-phosphate, N-acetylgalactosamine. Other derivatives include N-acetylglucosamine 3-acetate, N-acetylglucosamine 4-acetate, N-acetylglucosamine 6-acetate, N-acetylglucosamine 3,4 diacetate, N-acetylglucosamine 3,6 diacetate, N-acetylglucosamine 4,6 diacetate, and N-acetylglucosamine 3,4,6 triacetate. Suitable analogs and derivatives are described, e.g., in US 20170042919, which is incorporated herein by reference.

Alpha synuclein (aSyn or α-Syn) is a 140 amino-acid protein that was originally identified in association with synaptic vesicles in the presynaptic nerve terminal and has been shown to interact with membranes both in vitro and in vivo. It is highly abundant in the brain and also present in other tissues, including red blood cells. aSyn is a member of a protein family of synucleins, together with beta (β)- and gamma (γ)-synuclein. These proteins share a characteristic consensus sequence (KTKEGV) that is repeated about six times at the N-terminal part of the protein. β-synuclein shares the closest homology (90% homology in the N-terminus and 33% homology in the C-terminus) with aSyn.

Point mutations in the SNCA gene, encoding for aSyn, and multiplications of the SNCA locus have been identified in families with autosomal-dominant forms of Parkinson's disease (PD). Genome-wide association studies linked single-nucleotide polymorphisms in the SNCA gene with increased susceptibility to sporadic PD. Moreover, SNCA gene polymorphisms have also been associated with increased risk of multiple system atrophy (MSA).

In PD, aSyn is found as a major component of Lewy bodies and Lewy neurites, the hallmark protein inclusions made up primarily of insoluble and fibrillar aSyn protein. aSyn also accumulates in dementia with Lewy bodies (DLB) and MSA. In MSA, aSyn is found predominantly within oligodendrocytes as cytoplasmic inclusions. These disorders share the accumulation of aSyn aggregates as a pathological feature and are collectively known as synucleinopathies. As used herein, the term "synucleinopathy" refers to any disease associated with aSyn aggregates including Parkinson's Disease (PD), MSA, DLB and pure autonomic failure (PAF). In one embodiment, synucleinopathy refers to Parkinson's disease.

The universal feature of α-synucleinopathies is the presence of proteinaceous intracellular entities or bodies containing aggregates of α-synuclein (referred to herein as "α-synuclein aggregates" or "aSyn aggregates"). These bodies differ somewhat in appearance in different α-synucleinopathies, and are called Lewy bodies in PD and DLB, glial cytoplasmic inclusions in MSA and axonal spheroids in neuroaxonal dystrophies. Much evidence indicates that the mechanism underpinning α-synucleinopathies is the misfolding of α-synuclein into aggregates. In vitro studies have shown that α-synuclein aggregates (that is, oligomers) cause a series of secondary processes leading to neuroinflammation, neurodegeneration and cell death. See, Kim et al, Alzheimer's Research & Therapy 20146:73, incorporated by reference herein.

The term "antibody" or "antibodies" as used herein refers to all types of immunoglobulins, including IgG, IgM, IgA, IgD, and IgE, including antibody fragments. The antibody can be monoclonal or polyclonal and can be of any species of origin, including (for example) mouse, rat, rabbit, horse, goat, sheep, camel, or human, or can be a chimeric antibody. See, e.g., Walker et al., Molec. Immunol. 26:403 (1989). The antibodies can be recombinant monoclonal antibodies produced according to known methods, see, e.g., U.S. Pat. No. 4,474,893 or 4,816,567, which are incorporated herein by reference.

Antibody fragments include, for example, Fab, Fab', F(ab')$_2$, and Fv fragments; domain antibodies, bifunctional, diabodies; vaccibodies, linear antibodies; single-chain antibody molecules (scFV); and multispecific antibodies formed from antibody fragments. Such fragments can be produced by known techniques.

Antibodies useful herein may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Methods for humanizing non-human antibodies are well known in the art. See, e.g., the method of Winter and co-workers (Jones et al., Nature 321:522 (1986); Riechmann et al., Nature 332:323 (1988); Verhoeyen et al., Science 239:1534 (1988)), each of which is incorporated herein by reference.

The terms "administering" or "administration" refers to the process by which a therapeutically effective amount of compound[s] or a composition described herein are delivered to a patient for preventive or treatment purposes. Compound[s] and compositions are administered in accordance with good medical practices taking into account the patient's clinical condition, the site and method of administration, dosage, patient age, sex, body weight, and other factors known to physicians.

"Therapeutically effective amount" relates to the amount or dose of an active compound, composition, or combination therapy as described herein, e.g., GlcNAc, an analog or derivative thereof. A therapeutically effective amount of a compound, composition, or preparation can vary according to factors such as the disease state, age, sex, and weight of the individual, and the ability of the substance to elicit a desired response in the individual. Dosage regime may be adjusted to provide the optimum therapeutic response (e.g. beneficial effects). For example, several divided doses may be administered daily or the dose may be proportionally reduced as indicated by the exigencies of the therapeutic situation.

As used herein, pharmaceutically acceptable carrier, excipient, or diluent refers to a medium which does not interfere with the effectiveness or activity of an active ingredient and which is not toxic to the hosts to which it is administered. A carrier, excipient, or diluent includes binders, adhesives, lubricants, disintegrates, bulking agents, wetting or emulsifying agents, pH buffering agents, and miscellaneous materials such as absorbants that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease, the relapse of a disease after remission, or of one or more symptoms associated with such disease. The terms "treatment" and "therapeutically," refer to the act of treating, as "treating" is defined above.

It is to be noted that the term "a" or "an" refers to one or more. As such, the terms "a" (or "an"), "one or more," and "at least one" are used interchangeably herein.

While various embodiments in the specification are presented using "comprising" language, under other circumstances, a related embodiment is also intended to be interpreted and described using "consisting of" or "consisting essentially of" language. The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder" and "condition" are used interchangeably, to indicate an abnormal state in a subject.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made.

Methods of Treatment

Provided herein are methods of treating constipation in a subject in need thereof. Constipation refers to infrequent or difficult to pass bowel movements, sometimes associated with hard and/or dry stool. Constipation has various causes, ranging from illness to poor diet to certain medical conditions. It has been observed that patients afflicted with synucleinopathies experience constipation. For example, in Parkinson's Disease, the gastrointestinal system is impaired from both a motor and dysautonomic standpoint. In addition, it also plays an active part in the pathophysiological changes that underlie motor fluctuations through its effects on absorption of antiparkinsonian drugs. Fasano et al, Lancet Neurol 2015; 14: 625-39, which is incorporated herein by reference.

The pathological changes of Parkinson's disease are defined by abnormal α-synuclein accumulation in the brain in characteristic Lewy bodies or Lewy neurites. However, evidence for abnormal α-synuclein accumulation outside the brain, including throughout the enteric nervous system, is growing. It has been demonstrated that aggregated α-synuclein exists in the colon of non-PD individuals (Adler, et al. Submandibular gland needle biopsy for the diagnosis of Parkinson disease. Neurology, 2014; 82: 858-64), leading to the theory that in Parkinson's disease, α-synuclein might disaggregate and infiltrate the CNS as soluble α-synuclein oligomers. See, Fasano et al, Lancet, June 2015, 14:625-39. The extent of gastrointestinal dysfunction, with corresponding widespread enteric nervous system synucleinopathy, suggests that a disruption in the physiological function of α-synuclein might have a pivotal role in gastrointestinal dysfunction.

Thus, in one embodiment, a method of treating constipation in a subject having a synucleinopathy is provided. The method includes administering an effective amount of N-acetylglucosamine or an analog or derivative thereof. In one embodiment, the synucleinopathy is Parkinson's Disease. In another embodiment, the synucleinopathy is Lewy body dementia. In another embodiment, the synucleinopathy is multiple system atrophy (MSA). In another embodiment, the synucleinopathy is pure autonomic failure (PAF).

In another aspect, a method of treating constipation in a subject in need thereof is provided. The method includes administering an effective amount of N-acetylglucosamine or an analog or derivative thereof. In one embodiment, the constipation is a symptom of Crohn's disease. In another embodiment, the constipation is a symptom of colitis. In another embodiment, the constipation is a symptom of hypothyroidism. In another embodiment, the constipation is a symptom of medication. In another embodiment, the constipation is a symptom of poor diet. In another embodiment, the constipation is a symptom of pregnancy. In another embodiment, the constipation is a symptom of diabetes. In another embodiment, the constipation is a symptom of multiple sclerosis (MS). In another embodiment, the constipation is a medicinal side effect.

Treatment of constipation, in one embodiment, means an increase in the frequency of bowel movements. In another embodiment, treatment of constipation means an improvement of the water content of the stool, i.e., increase in water content.

A method of solubilizing alpha-synuclein aggregates in a subject having a synucleinopathy, said method comprising administering N-acetylglucosamine or an analog or derivative thereof, wherein motor function in the gut and central nervous system of the subject is normalized.

Also contemplated herein is the use of N-acetylglucosamine for decreasing or solubilizing alpha-synuclein aggregates in a subject in need thereof. It has been shown that alpha-synuclein without O-GlcNAcylation forms aggregates, while O-GlcNAcylation at amino acid 72 keeps alpha-synuclein in solution. Thus, the method includes administering an effective amount of N-acetylglucosamine or an analog or derivative thereof to decrease or solubilize alpha-synuclein aggregates. In one embodiment, the subject has a synucleinopathy selected from Parkinson's Disease, Lewy body dementia, multiple system atrophy (MSA) and pure autonomic failure (PAF). In one embodiment, the synucleinopathy is Parkinson's Disease.

In another aspect, a method of preventing aggregation of alpha-synuclein is provided. The method includes administering an effective amount of N-acetylglucosamine or an analog or derivative thereof Additional Components In some embodiments of the methods described herein, the GlcNAc, or analog or derivative thereof, is administered with an additional therapy. In one embodiment, the additional therapy is uridine. As used herein, "uridine" or "UMP" refers to uracil and any form thereof, including uridine monophosphate (UMP) or uracil. UMP has been shown to have restorative effects in PD when administered with docosahexaenoic acid. Cansev et al, Neurosci Res. 2008 November; 62(3): 206-209, which is incorporated herein by reference.

In addition, various therapies are known in the art for treatment of synucleinopathies, including Parkinson's Disease and are contemplated for use with the methods herein. Various treatments are also in development and clinical trials, and are contemplated for use with the methods herein. In one embodiment, the additional therapy is a dopaminergic therapy selected from L-DOPA, inhibitors of aromatic amino acid decarboxylase (AADC) including carbidopa or benserazide, catechol-O-methyltransferase (COMT) inhibitors including poicapone, Piribedil, pramipexole, pramipexole extended release, ropinirole, rotigotine, cabergoline, and pergolide, monoamine oxidase type B (MAOB) inhibitors including selegiline and rasagiline and safinamide, dopamine agonists including rotigotine and apomorphine. In another embodiment, the additional therapy is a dopamine β-hydroxylase inhibitor. In one embodiment, the dopamine β-hydroxylase inhibitor is selected from disulfiram and nepicastat. See, DiCiano et al, Effects of disulfiram on choice behavior in a rodent gambling task: association with catecholamine levels, Psychopharmacology, 235:23-35 (October 2017), which is incorporated herein by reference.

In another embodiment, the additional therapy is a prokinetic drug such as macrogol or lubiprostone or resistant starch.

In another embodiment, the additional therapy is selected from nilotinib, affitope, ambroxol, insulin, Pyridostigmine bromide, fludrocortisone, liraglutide, lovastatin, and NPT200-11.

In another embodiment, the additional therapy is an agent or treatment used to treat constipation. Such agents include laxatives, fiber, osmotic agents, polyethylene glycol, and 5-ht4 agonists. In one embodiment, the additional therapy is a laxative such as a bulk laxative, osmotic agent, stimulant laxative, emollient or neuromuscular agent. Bulk laxatives include dietary fiber, psyllium, polycarbophil, methylcellulose, and carboxymethylcellulose. Osmotic agents include saline laxatives such as Magnesium, sulfate, potassium and phosphate salts; poorly absorbed sugars: Lactulose, sorbitol, mannitol, lactose, and glycerine suppositories; and polyethylene glycol. In one embodiment, the additional therapy is a stimulant laxative. Stimulant laxatives include surface-active agents including docusate and bile salts; diphenylmethane derivatives including phenolphthalein, bisacodyl, and sodium picosulfate; ricinoleic acid (castor oil); anthraquinones including senna, cascara sagrada, aloe, and rhubarb. In another embodiment, the laxative is an emollient such as mineral oil. In another embodiment, the laxative is a neuromuscular agent. In one embodiment, the neuromuscular agent is selected from a 5-HT4 agonist such as cisapride, norcisapride, prucalopride, and tegaserod; colchicine, misoprostol; a cholinergic agents such as bethanechol or neostigmine; an opiate antagonist such as naloxone or naltrexone; or recombinant methionyl human brain-derived neurotrophic factor (r-metHuBDNF) neurotropin-3. See, Portalatin and Winstead, Medical Management of Constipation, Clin Colon Rectal Surg. 2012 March; 25(1): 12-19, which is incorporated herein by reference.

In yet another embodiment, the additional therapy is an anti-synuclein antibody. In certain embodiments, the anti-synuclein antibody prevents or reduces formation of alpha-synuclein aggregates. In one embodiment, the anti-synuclein antibody is selected from BIIB054, PRX002/R07046015.

In another embodiment, the additional therapy is stem cell therapy or fetal tissue transplantation.

Dosage

The dosage of GlcNAc may be determined by the medical professional. In one embodiment of any of the methods described herein, the GlcNAc is administered in an amount from about 1.5 grams per day to about 15 grams per day. In another embodiment, the GlcNAc is administered in an amount from about 3 grams per day up to about 9 grams/day. In another embodiment, the GlcNAc is administered in an amount from about 3 grams per day up to about 6 grams/day. In another embodiment, the GlcNAc is administered in an amount of about 1 gram/day. In another embodiment, the GlcNAc is administered in an amount of about 2 grams/day. In another embodiment, the GlcNAc is administered in an amount of about 3 grams/day. In another embodiment, the GlcNAc is administered in an amount of about 4 grams/day. In another embodiment, the GlcNAc is administered in an amount of about 5 grams/day. In another embodiment, the GlcNAc is administered in an amount of about 6 grams/day. In another embodiment, the GlcNAc is administered in an amount of about 7 grams/day. In another embodiment, the GlcNAc is administered in an amount of about 8 grams/day. In another embodiment, the GlcNAc is administered in an amount of about 9 grams/day. In another embodiment, the GlcNAc is administered in an amount of about 10 grams/day. In another embodiment, the GlcNAc is administered in an amount of about 11 grams/day. In another embodiment, the GlcNAc is administered in an amount of about 12 grams/day. In another embodiment, the GlcNAc is administered in an amount of about 13 grams/day. In another embodiment, the GlcNAc is administered in an amount of about 14 grams/day. In another embodiment, the GlcNAc is administered in an amount of about 15 grams/day. Such dosage may be administered in one or more separate dosing units, one or more times per day. In one embodiment, the GlcNAc is administered once per day. In another embodiment, the GlcNAc is administered twice per day. In another embodiment, the GlcNAc is administered three times per day. In another embodiment, the GlcNAc is administered 4, 5 or 6 times per day.

The dosage of uridine may be determined by a medical professional. In one embodiment, uridine is provided as uridine monophosphate (UMP). In one embodiment, the UMP is administered in an amount of about 100 mg to about 10 grams per day. In another embodiment, the UMP is administered in an amount of about 200 mg/day. In another embodiment, the UMP is administered in an amount of about 300 mg/day. In another embodiment, the UMP is administered in an amount of about 400 mg/day. In another embodiment, the UMP is administered in an amount of about 500 mg/day. In another embodiment, the UMP is administered in an amount of about 600 mg/day. In another embodiment, the UMP is administered in an amount of about 700 mg/day. In another embodiment, the UMP is administered in an amount of about 800 mg/day. In another embodiment, the UMP is administered in an amount of about 900 mg/day. In another embodiment, the UMP is administered in an amount of about 1 gram/day. In another embodiment, the UMP is administered in an amount of about 2 grams/day. In another embodiment, the UMP is administered in an amount of about 3 grams/day. In another embodiment, the UMP is administered in an amount of about 4 grams/day. In another embodiment, the UMP is administered in an amount of about 5 grams/day. In another embodiment, the UMP is administered in an amount of about 6 grams/day. In another embodiment, the UMP is administered in an amount of about 7 grams/day. In another embodiment, the UMP is administered in an amount of about 8 grams/day. In another embodiment, the UMP is administered in an amount of about 9 grams/day. In another embodiment, the UMP is administered in an amount of about 10 grams/day. Such dosage may be administered in one or more separate dosing units, one or more times per day. In one embodiment, the UMP is administered once per day. In another embodiment, the UMP is administered twice per day. In another embodiment, the UMP is administered three times per day. In another embodiment, the UMP is administered 4, 5 or 6 times per day.

The dosages and regimens for the other therapies noted herein can be readily determined by the treating medical professional.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

Example 1: Safety and Efficacy of N-Acetylglucosamine on Motor and Constipation Symptoms in Parkinson's Disease: A Pilot Study Participants Participants were enlisted in a movement disorders outpatient clinic in Toronto, Canada. Inclusion criteria were a diagnosis of PD according to UK PD society brain bank criteria and chronic constipation that was not improved by laxatives. Exclusion criteria were the co-occurrence of conditions biasing results and/or changes of medications (including anti-constipation drugs).

Design

This was an open-label study that sought to evaluate the efficacy of GlcNAc (Villicote®, Wellesley Therapeutics Inc.) on PD patients with chronic constipation who have previously used laxatives to relieve symptoms of constipation, to little or no avail. Participants or their caregivers were interviewed over the phone and asked to answer a short questionnaire regarding motor-symptoms and bowel movements a week prior to taking Villicote and a week after taking Villicote. The self-reported assessments evaluated motor condition and dysfunction (fluctuation and dyskinesia) using section IV of the Unified Parkinson's Disease Rating Scale (UPDRS IV) [13] and asking about presence and frequency of delayed onset (Delayed ON) and Failure of "on" response (no ON); Perceived severity and improvement in of motor dysfunction, and constipation by means of both Patients' Global Impression-Severity (PGI-S) [14,15] and Patients' Global Impressions of Change (PGI-C) [16] scale accordingly. Severity of Constipation was also evaluated by means of questions 5 and 6 of SCOPA-AUT [17] and the Constipation Scoring System (CSS) [18]. In addition, side-effects experienced while on Villicote and qualitative feedback on the product was noted.

Results

Eight patients (89%) completed the study, and two did not take the prescribed medication. Their age and disease duration was 65.7±7.5 and 11.7±5.1 years, respectively. Mean UPDRS-III at study entry was 22.1±10.9.

Table 1 shows the effect of GlcNAc treatment at 1 month time point. Only significant effect was seen for CSS (Wilcoxon Signed Ranks Test: Z=−2.043, P=0.041), also depicted by FIG. 1. Table 2 shows the values of PGI-S and -I for motor fluctuations and constipations.

TABLE 1

|  | Before GlcNAc | After GlcNAc |
|---|---|---|
| UPDRS-IV | 3.9 ± 2.4 | 3.9 ± 2.4 |
| Delayed-ON | 0.1 ± 0.4 | 0.1 ± 0.4 |
| No-ON | 0.0 | 0.0 |
| CSS | 9.4 ± 6.1 | 6.5 ± 3.9 |
| SCOPA-AUT | 3.9 ± 1.9 | 3.1 ± 1.7 |

TABLE 2

| PGI-S Fluctuation | 0.8 ± 0.9 |
|---|---|
| PGI-I Fluctuation | 0 |
| PGI-S Constipation | 2.8 ± 1.3 |
| PGI-I Constipation | 1.6 ± 1.4 |

CONCLUSIONS

This preliminary study supports that GlcNAc is a well-tolerated and effective anti-constipation agent in PD patients. The inclusion of patients failing drugs for constipation further support this notion. No effect was observed in terms of motor functions although the design and short follow-up duration of the study might not help investigating this particular aspect.

All publications cited in this specification are incorporated herein by reference, as well as U.S. Provisional Patent Application No. 62/640,431. While the invention has been described with reference to particular embodiments, it will be appreciated that modifications can be made without departing from the spirit of the invention. Such modifications are intended to fall within the scope of the appended claims.

REFERENCES

1. Wellesley Therapeutics Inc
2. Salvatore, S., Heuschkel, R., Tomlin, S., et al (2000) A pilot study of N-acetyl glucosamine, a nutritional substrate for glycosaminoglycan synthesis, in paediatric chronic inflammatory bowel disease. Alimentary Pharmacology & Therapeutics, 14: 1567-1579.
3. Seidman E, Bernotti S, Levy E (2002) Nutritional Modulation of Gut Inflammation. Clinical Nutrition: Early Intervention D. Labadarios; C. Pichard (eds), Nestle Nutrition Workshop Series Clinical & Performance Program 7: 41-65.
4. Zhu A, Patel I, Hidalgo M, Gandhi V (2015). N-Acetyl-glucosamine for Treatment of Inflammatory Bowel Disease. Natural Medicine Journal 7(4).
5. Salvatore S, Heuschkel R, Tomlin S, et al. A pilot study of N-acetyl glucosamine, a nutritional substrate for glycosaminoglycan synthesis, in paediatric chronic inflammatory bowel disease. Aliment Pharmacol Ther 2000; 14(12):1567-1579.
6. Henchcliffe C, Beal M F (2008) Mitochondrial biology and oxidative stress in Parkinson disease pathogenesis. Nat Clin Pract Neurol 4: 600-609.
7. Wang Z, Udeshi N D, O'Malley M, Shabanowitz J, Hunt D F, Hart G W (2010) Enrichment and site mapping of O-linked N-acetylglucosamine by a combination of chemical/enzymatic tagging, photochemical cleavage, and electron transfer dissociation mass spectrometry. Mol Cell Proteomics. 9(1):153-160.
8. Jennifer A. Groves, Albert Lee, Gokben Yildirir, Natasha E. Zachara. (2013) Cell Stress and Chaperones, 18(5): 535-558.
9. Fasano A. Visangi N., Liu L., Lang A Pfeiffer R. (2015) Gastrointestinal dysfunction in Parkinson's disease. *Lancet Neurol.* 14: 625-639.
10. Kim, J.-S., & Sung, H.-Y. (2015) Gastrointestinal Autonomic Dysfunction in Patients with Parkinson's Disease. Journal of Movement Disorders, 8(2), 76-82.
11. Ueki, A., & Otsuka, M. (2004) Life style risks of Parkinson's disease: Association between decreased water intake and constipation. Journal of Neurology, 251(7): 18-23.
12. Barone P, Antonini A, Colosimo C, et al. (2009) The PRIAMO study: a multicenter assessment of nonmotor symptoms and their impact on quality of life in Parkinson's disease. Mov Disord. 24: 1641-1649.
13. Fahn S, Elton R, Committee. MotUD (1987) Recent developments in Parkinson's disease. Folorham Park, N.J.: Macmillan Health Care Information.
14. Viktrup, L, Hayes, R. P, Wang, P, and Shen W (2012) Construct validation of patient global impression of severity (PGI-S) and improvement (PGI-I) questionnaires in the treatment of men with lower urinary tract symptoms secondary to benign prostatic hyperplasia. BMC Urol. 12, 30.
15. Tincello D, Owen R, Slack M, Abrams K (2013) Validation of the Patient Global Impression scales for use in detrusor overactivity: secondary analysis of the RELAX study. BJOG; 120:212-216
16. Hurst H, Bolton J (2004) Assessing the clinical significance of change scores recorded on subjective outcome measures. Journal of Manipulative Physiological Therapeutics (IMPT). 27:26-35.
17. Visser M, Marinus J, Stiggelbout A M, Van Hilten J J (2004) Assessment of autonomic dysfunction in Parkinson's disease: the SCOPA-AUT. Mov Disord. 19:1306-12.
18. Agachan F, Chen T, Pfeifer J, Reissman P, Wexner S D (1996) A constipation scoring system to simplify evaluation and management of constipated patients. Dis Colon Rectum. 39: 681-5

What is claimed is:

1. A method of treating constipation in a subject having a synucleinopathy, said method comprising administering uridine monophosphate (UMP) and an effective amount of N-acetylglucosamine, thereby alleviating constipation that is a symptom of the synucleinopathy in the subject.

2. The method of claim 1, wherein the synucleinopathy is selected from Parkinson's Disease, Lewy body dementia, multiple system atrophy (MSA) and pure autonomic failure (PAF).

3. The method of claim 2, wherein the synucleinopathy is Parkinson's Disease.

4. A method of solubilizing alpha-synuclein aggregates in a subject having a synucleinopathy, said method comprising administering N-acetylglucosamine, wherein motor function in the gut and central nervous system of the subject is normalized.

5. The method of claim 4, further comprising administering Uridine monophosphate (UMP).

6. The method of claim 4, further comprising administering an additional therapy.

7. The method of claim 6, wherein the additional therapy is a dopaminergic therapy selected from L-DOPA, inhibitors of aromatic amino acid decarboxyalse (AADC) including carbidopa or benserazide, catechol-O-methyltransferase (COMT) inhibitors including poicapone, Piribedil, pramipexole, pramipexole extended release, ropinirole, rotigotine, cabergoline, and pergolide, monoamine oxidase type B (MAOB) inhibitors including selegiline and rasagiline and safinamide, dopamine agonists including rotigotine and apomorphine.

8. The method of claim 6, wherein the additional therapy is a pro-kinetic drug selected from macrogol or lubiprostone or resistant starch.

9. The method of claim 6, wherein the additional therapy is selected from nilotinib, affitope, ambroxol, insulin, Pyridostigmine bromide, fludrocortisone, liraglutide, lovastatin, and NPT200-11.

10. The method of claim 6, wherein the additional therapy is an anti-synuclein antibody.

11. The method of claim 10, wherein the anti-synuclein antibody prevents or reduces formation of alpha-synuclein aggregates.

12. The method of claim 11, wherein the anti-synuclein antibody is selected from BIIB054, PRX002/R07046015.

13. The method of claim 6, wherein the additional therapy is stem cell therapy or fetal tissue transplantation.

14. A method of decreasing alpha-synuclein aggregates in a subject in need thereof, said method comprising administering an effective amount of N-acetylglucosamine.

15. The method of claim 14, wherein the subject has a synucleinopathy selected from Parkinson's Disease, Lewy body dementia, multiple system atrophy (MSA) and pure autonomic failure (PAF).

16. The method of claim 15, wherein the synucleinopathy is Parkinson's Disease.

17. The method of claim 14, further comprising administering Uridine monophosphate (UMP).

18. The method of claim 14, further comprising administering an additional therapy.

19. The method of claim 18, wherein the additional therapy is a dopaminergic therapy selected from L-DOPA, inhibitors of aromatic amino acid decarboxyalse (AADC) including carbidopa or benserazide, catechol-O-methyltransferase (COMT) inhibitors including poicapone, Piribedil, pramipexole, pramipexole extended release, ropinirole, rotigotine, cabergoline, and pergolide, monoamine oxidase type B (MAOB) inhibitors including selegiline and rasagiline and safinamide, dopamine agonists including rotigotine and apomorphine.

20. The method of claim 18, wherein the additional therapy is a pro-kinetic drug selected from macrogol or lubiprostone or resistant starch.

21. The method of claim 18, wherein the additional therapy is selected from nilotinib, affitope, ambroxol, insulin, Pyridostigmine bromide, fludrocortisone, liraglutide, lovastatin, and NPT200-11.

22. The method of claim 18, wherein the additional therapy is an anti-synuclein antibody.

23. The method of claim 22, wherein the anti-synuclein antibody prevents or reduces formation of alpha-synuclein aggregates.

24. The method of claim 23, wherein the anti-synuclein antibody is selected from B1113054, PRX002/R07046015.

25. The method of claim 18, wherein the additional therapy is stem cell therapy or fetal tissue transplantation.

26. The method of claim 18, wherein the additional therapy is a dopamine β-hydroxylase inhibitor.

27. The method of claim 26, wherein the dopamine β-hydroxylase inhibitor is selected from disulfiram and nepicastat.

28. The method of claim 1, wherein the N-acetylglucosamine is administered in an amount from about 1.5 grams per day to about 15 grams per day.

29. The method of claim 4, wherein the N-acetylglucosamine is administered in an amount from about 1.5 grams per day to about 15 grams per day.

30. The method of claim 14, wherein the N-acetylglucosamine is administered in an amount from about 1.5 grams per day to about 15 grams per day.

\* \* \* \* \*